United States Patent [19]
Curtze et al.

[11] Patent Number: 5,399,559
[45] Date of Patent: Mar. 21, 1995

[54] FUNGICIDAL INDOLE DERIVATIVES

[75] Inventors: Jürgen Curtze, Geisenheim; Guido Albert, Hackenheim, both of Germany

[73] Assignee: Shell Research Limited, Waterloo, United Kingdom

[21] Appl. No.: 71,894

[22] Filed: Jun. 3, 1993

[30] Foreign Application Priority Data

Jun. 5, 1992 [EP] European Pat. Off. ........... 92109525

[51] Int. Cl.$^6$ ............... C07D 233/60; C07D 211/14; A61K 31/535
[52] U.S. Cl. .................... 514/235.2; 514/323; 514/397; 544/143; 546/201; 548/312.1
[58] Field of Search .......... 514/235.2, 323, 397; 544/143; 546/201; 548/312.1

[56] References Cited

U.S. PATENT DOCUMENTS 3,634,402  1/1972  Yamamoto et al. .......... 260/239.3
4,659,731  4/1987  Bigg et al. ...................... 514/397

FOREIGN PATENT DOCUMENTS 1305458  2/1970  United Kingdom ............ 548/312.1

OTHER PUBLICATIONS

CA 74(11): 53391n Synthesis . . . Compounds. Kollenz et al., p. 328, 1971.
CA 76(23): 140915w 7-Cloro- . . . Hydrochlorides. Yamamoto et al., p. 498, 1972.
CA 84(13): 89999n 1-Phenyl- . . . Derivatives, Fauran et al., p. 513, 1976.
CA 107(5): 39814w 2-Imidazolinyl . . . Compositions. Bigg et al., p. 703, 1987.
CA 108(9): 75248u Indoles, IV . . . -pyrido [3,4-b] indoles. El-Gendy et al., p. 668, 1988.
CA 111(1): 7305x Novel . . . Agents. Unangst et al., p. 700, 1989.

*Primary Examiner*—Mary C. Lee
*Assistant Examiner*—Joseph K. McKane

[57] ABSTRACT

The invention relates to fungicidal compositions which comprise a carrier and, as active ingredient, an indole derivative of the formula

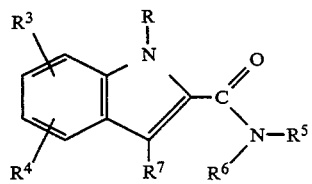

in which R is a substituted phenyl group; $R^3$ and $R^4$ independently are hydrogen or halogen or an optionally substituted alkyl, alkoxy, cycloalkyl, phenyl or phenoxy group; $R^5$ and $R^6$ independently are hydrogen atom or an optionally substituted alkyl, alkoxy, cycloalkyl, phenyl or heterocyclyl group or $R^5$ and $R^6$ together with the interjacent nitrogen atom represent a heterocyclyl group; and $R^7$ is hydrogen or alkyl group; and their use as fungicides. Certain of the above mentioned indole derivatives are novel and a process for the preparation of these compounds is also provided.

10 Claims, No Drawings

FUNGICIDAL INDOLE DERIVATIVES

FIELD OF THE INVENTION

The present invention relates to certain indole derivatives, processes for their preparation, compositions containing such compounds and their use as fungicides for the control of phytopathogenic fungi.

BACKGROUND OF THE INVENTION

Indole derivatives having specific useful activities are well known. For instance, in French patent FR 2260332 certain 3-substituted derivatives of 1-phenyl-2-aminocarbonylindole having pharmaceutical activity are described. In German patent application DE 2008692 certain 3-aminocarbonylindole derivatives having herbicidal and pharmaceutical activity are described. From Japanese patent applications J5 0070357 and J5 0070358 1,3-disubstituted 2-aminoacetylindole derivatives and 1,3-disubstituted 2-(3-amino-propionyl-)indole derivatives are known. These derivatives have antifungal as well as pharmaceutical activity. Additionally, DE 1966206 discloses 5-chloro-1-(2-flurophenyl)-3-methyl-1H-indole-2-carboxamide as an intermediate in the preparation of certain 1,4-benzodiazepines which are useful as pharmaceuticals. There is no indication that this compound has any fungicidal activity.

It has now been found that certain new indole derivatives, especially indole derivatives which are unsubstituted at the 3-position, show excellent fungicidal activity, particularly against *Phytophthora infestans* and *Plasmopora viticola*.

DESCRIPTION OF THE INVENTION

According to the present invention there is, therefore, provided a fungicidal composition which comprises a carrier and, as active ingredient, the compound of the general formula

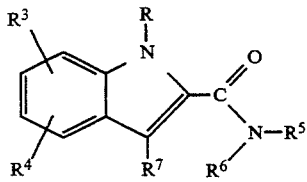

in which R is a substituted phenyl group; $R^3$ and $R^4$ independently are hydrogen or halogen or an optionally substituted alkyl, alkoxy, cycloalkyl, phenyl or phenoxy group; $R^5$ and $R^6$ are hydrogen or an optionally substituted alkyl, alkoxy, cycloalkyl, phenyl or heterocyclyl group or $R^5$ and $R^6$ together with the interjacent nitrogen atom represent a heterocyclyl group; and $R^7$ is hydrogen or alkyl group.

When the compounds in the compositions of this invention contain an alkyl or alkoxy substituent group, the group is linear or branched and contains up to 12, preferably up to 6 and especially up to 4, carbon atoms. A cycloalkyl group contains from 3 to 8, preferably 3 to 6, carbon atoms. A heterocyclyl group is any saturated or unsaturated ring system containing at least one heteroatom, 3- to 6-membered rings being preferred and 5- and 6-membered rings being especially preferred. Nitrogen, oxygen- and sulphur-containing heterocyclic rings, such as pyrrolidine, pyrrole, pyrroline, pyrazole, imidazole, triazole, tetrazole, pyrazoline, pyridine, piperidine, dihidropyridazine, tetrahydropyridazine, pyrimidine, dihydropyrimidine, tetrahydropyrimidine, dihydropyrazine, tetrahydropyrazine, oxazoline, morpholine, dihydrothiazine, tetrahydrothiazine, piperazine, furan, pyran and thiophene, are particularly preferred.

When any of the foregoing substituents are substituted, the substituent groups which are present are any one or more of those customarily employed in the development of pesticidal compounds and/or the modification of such compounds to influence their structure/activity, persistence, penetration or other property. Specific examples of such substituents include, for example, halogen, nitro, cyano, hydroxyl, alkyl, haloalkyl, alkoxy, haloalkoxy, hydroxyalkyl, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy, benzyl, benzyloxy, alkylenedioxy and cycloalkyl, especially cyclopropyl, groups. Typically, up to 3 substituents are present. When any of the foregoing substituents is or contains an alkyl substituent group, the group is linear or branched and contains up to 12, preferably up to 6, and especially up to 4, carbon atoms. When any of the foregoing substituents are or contain a cycloalkyl moiety, the cycloalkyl moiety may itself be substituted by one or more halogen atoms, nitro, cyano, alkyl, haloalkyl, alkoxy or haloalkoxy groups. Generally, substituents of alkyl, alkenyl, cycloalkyl and phenyl groups are preferably halogen, methoxy, nitro, amino, cyano and, in the case of cycloalkyl and phenyl, also methyl and trifluoromethyl.

It is preferred that R is a phenyl group substituted by one or more substituents selected from halogen atoms, nitro, cyano, hydroxyl, $C_{1-14}$ alkyl, $C_{1-4}$ haloalkyl, $C_{1-4}$ alkoxy, $C_{1-4}$ haloalkoxy, hydroxy-$C_{1-4}$ alkyl, amino, $C_{1-4}$ alkanoyl, carbamoyl and $C_{1-4}$ alkylenedioxy groups.

More preferably, R is a phenyl group substituted by one or more substituents selected from halogen, nitro, cyano, hydroxyl, $C_{1-4}$ alkyl, $C_{1-4}$ alkoxy, hydroxy-$C_{1-4}$ alkyl, amino, $C_{1-4}$ alkanoyl, carbamoyl and $C_{1-4}$ alkylenedioxy groups.

It is especially preferred that R is a phenyl group substituted by one or two $C_{1-4}$ alkoxy, especially methoxy or ethoxy, groups. Most preferably, R is a 3,4-dimethoxyphenyl group.

Preferably, $R^3$ and $R^4$ independently are hydrogen or halogen, an optionally substituted $C_{1-10}$ alkyl, $C_{1-10}$ alkoxy, $C_{3-8}$ cycloalkyl, phenyl or phenoxy group.

It is preferred that $R^3$ and $R^4$ independently are hydrogen or halogen or $C_{1-6}$ alkyl, $C_{1-6}$ alkoxy, $C_{3-8}$ cycloalkyl, phenyl or phenoxy group, each group being optionally substituted by one or more substituents selected from halogen and phenyl groups.

More preferably, $R^3$ and $R^4$ independently are hydrogen or halogen or a $C_{1-4}$ alkyl, $C_{1-4}$ alkoxy, $C_{3-36}$ cycloalkyl, phenyl or phenoxy group, each group being optionally substituted by one or more substituents selected from halogen, especially fluorine and chlorine, and phenyl groups.

Even more preferably, $R^3$ and $R^4$ independently are hydrogen, fluorine or chlorine, a $C_{1-14}$ alkyl group or a $C_{1-4}$ alkoxy group. It is especially preferred that $R^4$ is hydrogen and $R^3$ is hydrogen, fluorine or chlorine or a $C_{1-4}$ alkyl group, $R^3$ even more preferably being hydrogen, a 5- or 6-chloro or a n-$C_{1-4}$ alkyl group with substitution at the 5-position being especially preferred.

Preferably, $R^5$ and $R^6$ independently are hydrogen, $C_{1-6}$ alkyl, $C_{1-6}$ alkoxy, $C_{3-8}$ cycloalkyl or phenyl group or a 5- to 6-membered heterocyclic ring or $R^5$ and $R^6$ together with the interjacent nitrogen atom represent a 5- to 6-membered heterocyclic ring, each group or ring being optionally substituted by one or more substituents selected from halogen, $C_{3-6}$ cycloalkyl, halo-$C_{3-6}$ cycloalkyl and phenyl groups.

More preferably, $R^5$ and $R^6$ independently are hydrogen, a $C_{1-4}$ alkyl, $C_{1-4}$ alkoxy, $C_{3-6}$ cycloalkyl, phenyl or morpholinyl group or $R^5$ and $R^6$ together with the interjacent nitrogen atom represent an imidazolyl, piperidyl or morpholinyl group, each group being optionally substituted by one or more substituents selected from halogen, especially fluorine or chlorine, atoms, cyclopropyl, dichlorocyclopropyl and phenyl groups.

It is particularly preferred that $R^5$ and $R^6$ together with the interjacent nitrogen atom are a piperidyl or morpholinyl group, each group being optionally substituted by one or two halogens, especially fluorine. Most preferably, $R^5$ and $R^6$ together with the interjacent nitrogen atom are a morpholinyl group.

It is also preferred that $R^7$ is hydrogen or $C_{1-14}$ alkyl, especially a methyl, group. It is especially preferred that $R^7$ is hydrogen.

A particularly preferred sub-group of compounds of formula I is that in which R is nitrophenyl, cyanophenyl, hydroxyphenyl, hydroxymethylphenyl, aminophenyl, ethanoylphenyl, carbamoylphenyl, methylenedioxyphenyl, fluoro-methyl-phenyl, fluoro-methoxy-phenyl, fluoro-amino-phenyl, difluoro-amino-phenyl, chloro-amino-phenyl, dichloro-amino-phenyl, hydroxyl-methoxy-phenyl, methyl-methoxy-phenyl, methyl-amino-phenyl, ethyl-aminophenyl or dimethoxyphenyl group; $R^3$ is hydrogen, fluorine, chlorine or bromine or a methyl, ethyl, propyl, butyl, trifluoromethyl, methoxy, ethoxy, propoxy, butoxy, benzyloxy, cyclohexyl, phenyl or chlorophenoxy group; $R^4$ is hydrogen; $R^5$ is methyl, ethyl, propyl, butyl, trifluoroethyl, cyanomethyl, dichlorocyclopropylmethyl, benzyl, methoxy, cyclopropyl, cyclohexyl, phenyl or morpholinyl group; $R^6$ is hydrogen or a methyl, ethyl or propyl group; or $R^5$ and $R^6$ together with the interjacent nitrogen atom is an imidazolyl, piperidyl or morpholinyl group; and $R^7$ is hydrogen or a methyl group.

A method of making a composition as defined above is also provided which comprises bringing a compound of formula I as defined above into association with at least one carrier. Such a composition may contain a single compound or a mixture of several compounds of the invention.

A composition according to the invention preferably contains from about 0.5% to about 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier is a solid or a liquid, including a material which is normally gaseous but which has been compressed to form a liquid, and any of the carriers normally used in formulating fungicidal compositions may be used.

Suitable solid carriers include natural and synthetic clays and silicates, for example, natural silicas such as diatomaceous earths; magnesium silicates, for example, talcs; magnesium aluminum silicates, for example attapulgites and vermiculites; aluminum silicates, for example, kaolinites, montmorillonites and micas; calcium carbonate; calcium sulphate; ammonium sulphate; synthetic hydrated silicon oxides and synthetic calcium or aluminum silicates; inert elements, for example, carbon and sulphur; natural and synthetic resins, for example, coumarone resins, polyvinyl chloride, and styrene polymers and copolymers; solid polychlorophenols; bitumen; waxes, for example, beeswax, paraffin wax, and chlorinated mineral waxes; and solid fertilizers, for example, superphosphates.

Suitable liquid carriers include water; alcohols, for example, isopropanol and glycols; ketones, for example, acetone, methyl ethyl ketone, methyl isobutyl ketone and cyclohexanone; ethers; aromatic or araliphatic hydrocarbons, for example, benzene, toluene and xylene; petroleum fractions, for example, kerosene and light mineral oils; chlorinated hydrocarbons, for example, carbon tetrachloride, perchloroethylene and trichloroethane. Mixtures of different liquids are often suitable.

Fungicidal compositions are often formulated and transported in a concentration form which is subsequently diluted by the user before application. The presence of small amounts of a carrier which is a surface-active agent facilitates this process of dilution. Thus, preferably at least one carrier in a composition according to the invention is a surface-active agent. For example, the composition may contain at least two carriers, at least one of which carriers is a surface-active agent.

A surface-active agent may be an emulsifying agent, a dispersing agent or a wetting agent, either nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example, p-octylphenol or p-octylcresol, with ethylene oxide and/or propylene oxide; sulphates or sulphonates of these condensation products; alkali or alkaline earth metal salts, preferably sodium salts, or sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention are formulated as wettable powders, dusts, granules, solutions, emulsifiable concentrates, emulsions, suspension concentrates or aerosols. Wettable powders usually contain 25%, 50% or 75% w of active ingredient and usually contain, in addition to solid inert carrier, 3% to 10% w of a dispersing agent and, where necessary, up to 10% w of stabilizer(s) and/or other additives such as penetrants or stickers. Dusts are usually formulated as a dust concentrate having a similar composition to that of a wettable powder but without a dispersant, and may be diluted in the field with further solid carrier to give a composition usually containing 0.5% to 10% w of active ingredient. Granules are usually prepared to have a size between 10 BS mesh and 100 BS mesh (1.676 mm–0.152 mm), and are manufactured by agglomeration or impregnation techniques. Generally, granules will contain 0.5% to 75% w active ingredient and up to 10% w of additives such as stabilizers, surfactants, slow release modifiers and binding agents. The so-called "dry flowable powders" consist of relatively small granules having a relatively high concentration of active ingredient. Emulsifiable concentrates usually contain, in addition to a solvent and, when necessary, cosolvent, 1% to 50% w/v active ingredient, 2% to 20% w/v emulsifiers and up to 20% w/v of other additives such as stabilizers, penetrants and corrosion inhibitors. Suspension concentrates are usually compounded so as to obtain a stable, non-sedimenting flowable product and usually contain 10% to 75% w active ingredient, 0.5% to 15% w of dispersing agents, 0.1% to 10% w of suspending agents such as protective colloids and thixotropic agents, up to 10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example, compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example, other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The present invention still further provides the use as a fungicide of a compound of the general formula I as defined above or a composition as defined above, and a method for combating fungus at a locus, which comprises treating the locus, which may be, for example, plants subject to or subjected to fungal attack, seed of such plants or the medium in which such plants are growing or are to be grown, with such a compound or composition.

Certain of the compounds of formula I as defined above are novel. Accordingly, the invention also provides a compound of the formula I as previously defined with the proviso that, when R represents a 2-fluorophenyl group, each of $R^4$, $R^5$ and $R^6$ is hydrogen and $R^7$ is a methyl group, then $R^3$ does not represent a chlorine atom substituted at the 5-position of the indole ring.

The present invention also provides a process for the preparation of a compound of the formula I as defined above which comprises reacting a compound of the formula

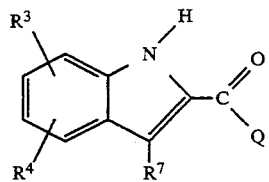

(II)

in which $R^3$, $R^4$ and $R^7$ are as defined above and Q is the group —$NR^5R^6$ or the group —$OR^8$ where $R^5$ and $R^6$ are as defined above and $R^8$ is an alkyl or alkenyl group, with a compound of the formula R—Hal (III)

in which R is as defined above and Hal is halogen; and, when Q represents a group —$OR^8$ in the compound of formula II, reacting the compound so obtained with a compound of the formula $HNR^5R^6$ (IV)

in which $R^5$ and $R^6$ are as defined above.

The conversion of the compound obtained by reaction of a compound with the formula II in which Q represents a group —$OR^8$ and a compound of the formula III comprises hydrolysis of the ester and, preferably, activation of the acid so obtained using an activating agent, followed by the reaction of the activated intermediate with an amine of the formula IV. The activating agent is preferably N,N'-carbonyldiimidazole or an ester of chloroformic acid, e.g., a $C_{1-4}$ alkyl ester. Another possibility is the direct conversion of the ester with the amine of the formula IV under the influence of a catalyst, e.g., a strong base, such as sodium or potassium alcoholates such as sodium methoxide. $R^8$ preferably is a $C_{1-6}$ alkyl group.

The first step of the preparation process, which process as such is known in the art, see for instance H. Ishi et al., Chem. Pharm. Bull., 39, 572–578 (1991), is carried out by reaction of an appropriately substituted indole-2-carboxylic ester or amide of the formula II with an appropriately substituted aromatic halide of the formula III in the presence of a suitable catalyst. Suitable catalysts are salts of transition elements in which the valence of the element is not the maximum value, especially copper salts. Preferably, halides are used, especially copper (I) bromide. In order to neutralize the hydrogen halide which is formed during the reaction, suitably a base is added to the reaction mixture. Very suitably carbonates or bicarbonates derived from alkali metals or alkaline earth metals are used. Alternatively, organic bases, such as pyridine, may be added to the reaction mixture. The reaction is carried out in an inert organic solvent, e.g., aromatic solvents, especially nitrobenzene, toluene and xylene, at elevated temperatures. The temperature is suitably between 40° C. and 180° C., preferably between 100° C. and 140° C.

The product is isolated and optionally purified, whereafter, if necessary, the ester group is converted into the amide group by hydrolysis followed by reaction with the appropriate amine, suitably after activation of the acid. Activation is suitably carried out by reaction with activating reagents, for instance chlorinating or brominating agents, such as phosphorus oxychloride, thionyl chloride and sulphuryl chloride, N,N'-carbonyldiimidazole or esters of chloroformic acid.

Direct conversion under the influence of a basic catalyst is also possible. The hydrolysis reaction suitably is carried out in a protic solvent, for instance, a mixture of an alcohol and water. Acid or base may be added to improve the reaction rate. After isolation and drying of the product, optionally followed by purification, the product is reacted with the activating agent under reaction conditions well known in the art, whereafter the activated product is reacted with the appropriate amine compound, also at reaction conditions well known in the art.

In the case where the starting product of the formula II is a carboxylic amide compound it will be appreciated that this compound may be obtained by reaction of the corresponding ester in the same way as described hereinbefore.

Compounds of formula II in which Q is —OR$^8$ and compounds of formulae III and IV are known compounds or can be prepared by known processes or processes analogous to known processes.

The present invention is of wide applicability in the protection of crop plants against fungal attack. Typical crops which may be protected include vines, potatoes, tomatoes, tobacco, hops, salads and cucumber. The duration of protection is normally dependent on the individual compound selected, and also a variety of external factors, such as climate, whose impact is normally mitigated by the use of a suitable formulation.

The invention is further illustrated by the following examples.

EXAMPLE 1

Preparation of 1-(3,4-dimethoxyphenyl)indole-2-carboxic acid morpholide (R=3,4-(OCH$_3$)$_2$phenyl; R$^3$=R$^4$=R$^7$=H;
—NR$^5$R$^6$=morpholin-4-yl)

(a) Preparation of 1-(3,4-dimethoxyphenyl)indole-2-carboxylic acid ethyl ester

4-Bromoveratrole (8.8 g, 40 mmol), indole-2-carboxylic acid ethyl ester (1.9 g, 10 mmol), potassium carbonate (1.9 g), copper- (I) bromide (o.2 g), pyridine (2 ml) and nitrobenzene (10 ml) were stirred at 140° C. for 14 hours. After cooling to room temperature, the reaction mixture was applied onto a silica gel flash chromatography column (silica gel: 140 g). The column was subsequently eluted with toluene (500 ml), toluene/acetone (95:5, 500 ml) and toluene/acetone (90:10, 500 ml). 1-(3,4-Dimethoxyphenyl)indole-2-carboxylic acid ethyl ester was eluted with toluene/acetone (90:10) and gave colorless crystals upon evaporation of the solvent. The crystals were triturated with diisopropyl ether, collected by vacuum filtration and dried in the air. Yield: 3.0 g. (92% of theoretical yield) M.pt.: 126°–128° C. R$_f$ (toluene/acetone, 9:1)=0.53.

(b) Preparation of 1-(3,4-dimethoxyphenyl)indole-2-carboxylic acid 1-(3,4-Dimethoxyphenyl)indole-2 -carboxylic acid ethyl ester (2.5 g, 7.7 mmol) obtained in (a) above and potassium hydroxide (o.6 g, 10 mmol) in water (5 ml) and ethanol (10 ml) were refluxed for 3 hours. The solvent was then removed by evaporation and the residue dissolved in a small amount of water. 1-(3,4-Dimethoxyphenyl)indole-2 -carboxylic acid was precipitated as colorless amorphous material by dropwise addition of hydrochloric acid (5M), chilled to 10° C., collected by vacuum filtration and dried at 90° C. for 5 hours. Yield: 2.2 g (96% of theoretical) M.pt.: 240-245° C.

(c) Preparation of 1-(3,4-Dimethoxyphenyl)indole-2-carboxylic acid 1-(3,4-Dimethoxyphenyl)indole-2-carboxylic acid (2.2 g, 7.4 mmol) obtained in (b) above was stirred in tetrahydrofuran (15 ml) and N,N'-carbonyl-diimidazole (2.4 g, 15 mmol) was added whereupon a clear solution developed. The solution was refluxed for 30 minutes. After the solution had cooled to 20° C., morpholine (0.7 g, 8 mmol) was added dropwise and the reaction mixture first stirred at room temperature for 10 minutes, then under reflux for 30 minutes. The solvent was evaporated, the residue dissolved in toluene and washed twice with water. The organic layer was evaporated and the residue applied onto a flash chromatography column packed with silica gel (30 g). The column was subsequently eluted with toluene/acetone (9:1, 250 ml) and toluene/acetone (8:2. 250 ml). 1-(3,4-dimethoxyphenyl)indole-2-carboxylic acid morpholide was eluted with toluene/acetone (8:2) and gave a colorless viscous oil after evaporation of the solvent. Yield: 2.4 g (88.6% of theoretical R$_f$(toluene/acetone, 7:30)=0.43. The NMR spectra was consistent with the assigned structure.

EXAMPLES 2 to 78

By processes similar to those described in Example 1 above, further compounds according to the invention are prepared which are detailed in Table 1 below. In all the following examples, R$^4$ is hydrogen. In this Table the compounds are identified by reference to formula I. Melting 5 are given in Table IA below in which the compounds are identified by reference to the Example numbers. In each of the following examples, the H-NMR spectra is consistent with the assigned structure.

TABLE 1

| Ex. No. | R | R$^3$ | —NR$^5$R$^6$ | R$^7$ |
|---|---|---|---|---|
| 2 | 3,4-(OCH$_3$)$_2$ phenyl | H | imidazol-1-yl | H |
| 3 | " | H | —NH—$^i$C$_3$H$_7$ | " |
| 4 | " | H | —NH—C$_6$H$_5$ | " |
| 5 | " | H | —NH—$^n$C$_4$H$_9$ | " |
| 6 | " | H | —NH—CH$_3$ | " |
| 7 | " | H | —N(CH$_3$)—CH$_2$C$_6$H$_5$ | " |
| 8 | " | 5-Cl | morpholin-4-yl | " |
| 9 | " | 6-Cl | " | " |
| 10 | " | 5-Br | " | " |
| 11 | 3,4-(OCH$_3$)$_2$phenyl | 6-CF$_3$ | morpholin-4-yl | H |
| 12 | " | 6-CH$_3$ | " | " |
| 13 | " | 5-$^n$C$_4$H$_9$ | " | " |
| 14 | " | 5-O$^n$C$_4$H$_9$ | " | " |
| 15 | " | 5-O$^n$C$_3$H$_7$ | " | " |
| 16 | " | 5-C$_6$H$_5$ | " | " |
| 17 | " | 5-O(4-Cl | " | " |

TABLE 1-continued

| Ex. No. | R | $R^3$ | $-NR^5R^6$ | $R^7$ |
|---|---|---|---|---|
| | | phenyl) | | |
| 18 | " | H | $-N(CH_3)_2$ | " |
| 19 | " | H | $-N(CH_3)-C_2H_5$ | " |
| 20 | " | H | $-N(C_2H_5)_2$ | " |
| 21 | " | H | $-N(CH_3)-{}^nC_3H_7$ | " |
| 22 | " | H | $-N(CH_3)-{}^nC_4H_9$ | " |
| 23 | " | H | piperid-1-yl | " |
| 24 | 3,4-(OCH$_3$)$_2$phenyl | 5-CH$_3$ | morpholin-4-yl | H |
| 25 | " | 5-CH$_3$ | $-N(C_2H_5)_2$ | " |
| 26 | " | 5-CH$_3$ | $-N(CH_3)-{}^nC_3H_7$ | " |
| 27 | " | 5-CH$_3$ | $-N({}^nC_3H_7)_2$ | " |
| 28 | " | H | $-N(C_2H_5)-{}^iC_3H_7$ | " |
| 29 | " | H | $-N(CH_3)-CH_2CN$ | " |
| 30 | " | H | $-N(CH_3)OCH_3$ | " |
| 31 | " | H | $-NH-N\begin{pmatrix}\\ \\ \end{pmatrix}O$ | " |
| 32 | " | H | $-N(CH_3)-CH(CH_3)C_2H_5$ | " |
| 33 | " | H | $-N(CH_3)-CH_2-\triangleleft\genfrac{}{}{0pt}{}{Cl}{Cl}$ | " |
| 34 | " | H | $-NHCH_2CF_3$ | " |
| 35 | " | 5-${}^nC_4H_9$ | $-N(C_2H_5)_2$ | " |
| 36 | " | 5-F | morpholin-4-yl | " |
| 37 | " | 5-F | $-N(C_2H_5)_2$ | " |
| 38 | " | 5-C$_2$H$_5$ | morpholin-4-yl | " |
| 39 | " | 5-C$_2$H$_5$ | $-N(C_2H_5)_2$ | " |
| 40 | " | 5-OC$_2$H$_5$ | $-N(C_2H_5)_2$ | " |
| 41 | " | H | $-N(OCH_3)C_2H_5$ | " |
| 42 | " | 5-C(CH$_3$)$_3$ | morpholin-4-yl | " |
| 43 | " | 5-C(CH$_3$)$_3$ | $-N(C_2H_5)_2$ | " |
| 44 | " | H | $-N(C_2H_5)$-cyclohexyl | " |
| 45 | " | cyclohexyl | morpholin-4-yl | " |
| 46 | " | cyclohexyl | $-N(C_2H_5)_2$ | " |
| 47 | " | H | $-NH$-cyclopropyl | " |
| 48 | " | H | $-N(C_2H_5)$-cyclopropyl | " |
| 49 | " | H | $-N(CH_3)$-cyclopropyl | " |
| 50 | " | H | $-N(C_2H_5)-{}^nC_3H_7$ | " |
| 51 | " | H | $-N(C_2H_5)-{}^nC_4H_9$ | " |
| 52 | " | 5-OCH$_3$ | morpholin-4-yl | " |
| 53 | " | 5-OCH$_3$ | $-N(C_2H_5)_2$ | " |
| 54 | " | 5-CH(CH$_3$)$_2$ | $-N(C_2H_5)_2$ | " |
| 55 | " | 5-CH(CH$_3$)$_2$ | morpholin-4-yl | " |
| 56 | 3,4-(OCH$_3$)$_2$ phenyl | 5-Cl | $-N(C_2H_5)_2$ | H |
| 57 | " | 5-OCH$_2$C$_6$H$_5$ | morpholin-4-yl | " |
| 58 | " | 5-F | morpholin-4-yl | " |
| 59 | " | H | $-N(CH_3)-{}^iC_3H_7$ | " |
| 60 | 3,5-Cl$_2$,4-NH$_2$ phenyl | H | morpholin-4-yl | " |
| 61 | 3-OCH$_3$, 4-OH phenyl | H | " | " |
| 62 | 3,4-OCH$_2$O-phenyl | H | " | " |
| 63 | 3-CH$_3$,4-OCH$_3$ phenyl | H | " | " |
| 64 | 3-Cl,4-NH$_2$ phenyl | H | " | " |
| 65 | 3-F,4-NH$_2$ phenyl | " | " | " |
| 66 | 4-NH$_2$ phenyl | " | " | " |
| 67 | 3-F,4-CH$_3$ phenyl | " | " | " |
| 68 | 3,5-F$_2$,4-NH$_2$ phenyl | " | " | " |
| 69 | 4-CONH$_2$ phenyl | " | " | " |
| 70 | 4-COCH$_3$ phenyl | " | " | " |
| 71 | 3-C$_2$H$_5$, 4-NH$_2$ phenyl | " | " | " |
| 72 | 4-OH phenyl | " | " | " |
| 73 | 3-F, 4-OCH$_3$ phenyl | " | " | " |
| 74 | 4-CN phenyl | " | " | " |
| 75 | 4-CH$_2$OH phenyl | " | " | " |
| 76 | 4-NO$_2$ phenyl | " | " | " |
| 77 | 3,4-(OCH$_3$)$_2$ phenyl | " | " | $-CH_3$ |
| 78 | 3-CH$_3$, 4-NH$_2$ phenyl | " | " | H |

| TABLE 1A | |
|---|---|
| Example No. | M. pt (°C.) |
| 2 | oil |
| 3 | oil |
| 4 | oil |
| 5 | oil |

TABLE 1A-continued

| Example No. | M. pt (°C.) |
|---|---|
| 6 | oil |
| 7 | oil |
| 8 | 170-175 |
| 18 | oil |
| 19 | oil |
| 20 | oil |
| 21 | oil |
| 22 | oil |
| 23 | oil |

EXAMPLE 79

6-Chloro-1-(3,4-dimethoxyphenyl)indole-2-carboxylic acid morpholide (compound 9, alternative synthesis)

4-Bromoveratrole (5.7 g, 26 mmol), 6-chloroindole-2-carboxylic acid morpholide (1.7 g, 6.5 mmol), potassium carbonate (1.7 g), copper(I) bromide (0.2 g) in a mixture of pyridine (2 ml) and nitrobenzene was stirred at 140° C. for 14 hours. After cooling to room temperature, the reaction mixture was applied onto a flash chromatography column (silica gel, 140 g), Elution with toluene, toluene/acetone [9:1] and toluene/acetone [8:2] (500 ml each) gave 6-chloro-1-(3,4-dimethoxyphenyl)indole-2-carboxylic acid morpholide as brown oil. Yield: 2.1 g (81% of theoretical) $R_f$: 0.54 (toluene/acetone, 7:3). The H-NMR spectra was consistent with the assigned structure.

EXAMPLE 80

1-(3,4-Dimethoxyphenyl)indole-2-carboxylic acid —N-ethyl isopropyl amide (compound 28, alternative synthesis)

1-(3,4-Dimethoxyphenyl)indole-2-carboxylic acid (2.0 g, 6.8 mmol) was stirred in tetrahydrofuran (10 ml). Triethylamine (1 ml, 7.5 mmol) was added and the mixture was cooled to 0° C. Ethyl chloroformate (0.7 ml, 7 mmol) was added dropwise, followed by stirring for 30 minutes. N-ethyl isopropylamine (0.6 g, 7 mmol) in tetrahydrofuran was added, followed by stirring for 30 minutes and refluxing for 6 hours. The tetrahydrofuran was evaporated in vacuo, and the residue was dissolved in toluene. The toluene solution was washed with water, dried, evaporated in vacuo, applied onto a flash chromatography column (silica gel, 30 g) and eluted with toluene/acetone (9.5:0.5). The desired fractions were concentrated and the residue triturated with diisopropyl ether to give 1-(3,4-dimethoxyphenyl)indole-2-carboxylic acid N-ethyl isopropyl amide as white crystals which were then filtered and dried. Yield: 50 mg (2% of theoretical). $R_f$: 0.53 (toluene/acetone 7:3). The H-NMR spectra was consistent with the assigned structure.

Biological Testing

A) Determination of minimum inhibitory concentration (MIC value):

Ten test tubes (16×160 mm, with aluminum cap, Schott, Mainz FRG) per compound were filled with nutrient solution (V8-Juice, 3 ml) and autoclaved. After cooling down, sterile nutrient solution (3 ml) containing the active compound (200 μ/ml) was pipetted into the first tube and mixed. Then, half the content of the first tube (3 ml) was transferred to the second tube, mixed and, again, half the content of this tube transferred to the third and so on. By this means, the following series of test solutions was prepared:

| Tube No. | 1 | 2 | 3 | 4 | 5 | 6 | 7 | 8 | 9 | 10 |
|---|---|---|---|---|---|---|---|---|---|---|
| Concentration (a. i. μg/ml) | 100 | 50 | 25 | 12.5 | 6.25 | 3.13 | 1.56 | 0.78 | 0.39 | 0.2 |

The tubes were inoculated by transferring nutrient agar slices (5 mm diam.) from a *Phytophthora infestans* agar culture into the tubes. After an incubation time of 7 days at 18° C., the assessment was carried out by visual inspection of the test tubes. The lowest concentration in the test tubes without mycelium growth was recorded as the minimum inhibitory concentration (Table 2). All experiments were carried out together with a reference compound 3-(4-chlorophenyl)-3-(3,4-dimethoxyphenyl)acrylic acid morpholide).

TABLE 2

| Compound Example No. | M. I. C. Value | Reference Compound |
|---|---|---|
| 1 | 1.56 | (0.78) |
| 2 | >50 | (0.78) |
| 5 | >50 | (0.78) |
| 8 | 0.78 | (0.39) |
| 9 | 0.78 | (0.78) |
| 13 | 0.78 | (0.78) |
| 18 | 12.5 | (0.78) |
| 19 | 1.56 | (0.39) |
| 20 | 0.78 | (0.78) |
| 21 | 1.56 | (0.78) |
| 22 | 6.25 | (0.78) |
| 23 | >50 | (0.78) |
| 24 | 1.56 | (0.78) |
| 25 | 0.78 | (0.78) |
| 26 | 1.56 | (0.78) |
| 27 | >100 | (0.39) |
| 28 | 0.78 | (0.39) |
| 29 | 12.5 | (0.39) |
| 30 | 1.56 | (0.39) |
| 31 | 3.13 | (0.78) |
| 32 | 25 | (0.78) |
| 33 | 6.25 | (0.39) |
| 34 | >100 | (0.78) |
| 35 | 0.39 | (0.78) |
| 36 | 3.13 | (1.56) |
| 37 | 1.56 | (1.56) |
| 38 | 0.78 | (0.78) |
| 39 | 0.78 | (0.78) |
| 40 | 12.5 | (0.78) |
| 41 | 12.5 | (0.78) |
| 42 | 0.2 | (0.78) |
| 43 | 0.78 | (0.78) |
| 44 | 100 | (0.78) |
| 45 | 3.13 | (0.78) |
| 46 | 100 | (0.78) |
| 47 | >100 | (0.78) |
| 48 | 6.25 | (0.78) |
| 49 | 1.56 | (0.78) |
| 50 | 12.5 | (0.78) |
| 51 | 6.25 | (0.78) |
| 52 | 3.13 | (0.78) |
| 53 | 3.13 | (0.78) |
| 55 | 1.56 | (0.78) |
| 56 | 1.56 | (0.78) |
| 57 | 0.2 | (0.78) |
| 58 | 0.78 | (0.78) |
| 59 | 3.13 | (0.78) |
| 60 | 12.5 | (0.78) |
| 61 | 6.25 | (0.78) |
| 62 | >100 | (0.78) |
| 63 | 12.5 | (0.78) |
| 64 | 3.13 | (0.78) |
| 65 | 1.56 | (0.78) |
| 66 | 3.13 | (0.78) |
| 67 | 6.25 | (0.78) |
| 68 | 3.13 | (0.78) |

TABLE 2-continued

| Compound Example No. | M. I. C. Value | Reference Compound |
| --- | --- | --- |
| 69 | >100 | (0.78) |
| 70 | >100 | (0.78) |
| 71 | 25 | (0.78) |
| 72 | >100 | (0.78) |
| 73 | >100 | (0.78) |
| 74 | 100 | (0.78) |
| 75 | 50 | (0.78) |
| 76 | >100 | (0.78) |
| 77 | 50 | (0.78) |
| 78 | 3.13 | (0.78) |

B. Antisporulant activity against vine downy mildew (*Plasmopara viticola*; PVA)

The test is a direct antisporulant foliar spray. The lower surface of leaves of vine plants (cv Cabernet-Sauvignon), approximately 8 cm high, are inoculated with an aqueous suspension containing $2.5 \times 10^4$ zoosporangia/ml. The inoculated plants are kept for 24 hours at 21° C. in a high humidity cabinet, then 24 hours in the glasshouse at 20° C. and 40% R.H. Infected leaves are sprayed on their lower surfaces with the test compound in a 1:1 water/acetone mixture containing 0.04% Tween 20 (a polyoxyethylene sorbitant surfactant) and 600 ppm of the active ingredient. After drying, the plants are returned to the glasshouse at 20° C. and 40% R.H. for 96 hours and are then transferred to the high humidity cabinet for 24 hours to induce sporulation. The assessment (Table 3) is based on the percentage of the leaf area covered by sporulation compared with that on control leaves according to the table below.

0 = <50% activity
1 = 50–80% activity
2 = <80% activity

C. Direct protectant activity against tomato late blight (Phytophthora infestants; PIP)

The test is a direct protectant foliar spray. Tomato plants with two expanded leaves (cv First in the Field) are sprayed with the test compound as described above. After drying, the plants are kept for 24 hours in the glasshouse at 20° C. and 40% R.H. Then, the upper surfaces of the leaves are inoculated with an aqueous suspension containing $2 \times 10^5$ zoospores/ml. The inoculated plants are kept for 24 hours at 18° C. in a high humidity cabinet and 5 days at 15° C. and 80% R.H. in a growth chamber with 14 hours light/day. The assessment (Table 3) is based on the percentage of diseased leaf area compared with that on control leaves according to the below Table.

0 = <50% activity
1 = 50–80% activity
2 = <80% activity

TABLE 3

| Compound | PVA | PIP |
| --- | --- | --- |
| 1 | 2 | 2 |
| 3 | 0 | 0 |
| 4 | 0 | 0 |
| 5 | 0 | 0 |
| 6 | 0 | 0 |
| 7 | 0 | 0 |
| 8 | 2 | 2 |
| 9 | 2 | 2 |
| 19 | 2 | 2 |
| 20 | 2 | 2 |
| 21 | 2 | 2 |
| 22 | 2 | 2 |
| 23 | 0 | 0 |

TABLE 3-continued

| Compound | PVA | PIP |
| --- | --- | --- |
| 24 | 0 | 2 |
| 25 | 2 | 2 |
| 26 | 2 | 2 |
| 27 | 2 | 2 |
| 28 | 2 | 2 |
| 29 | 2 | 2 |
| 30 | 2 | 2 |
| 31 | 2 | 2 |
| 32 | 2 | 1 |
| 33 | 1 | 2 |
| 34 | 0 | 0 |
| 54 | | 2 |

What is claimed is:

1. A method of combatting fungus at a locus which comprises a compound of the formula

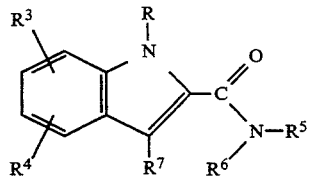

in which R is a substituted phenyl group; $R^3$ and $R^4$ independently are hydrogen or halogen or an optionally substituted alkyl, alkoxy, cycloalkyl, phenyl or phenoxy group; $R^5$ and $R^6$ independently are hydrogen or an optionally substituted alkyl, alkoxy, cycloalkyl, phenyl or heterocyclyl group or $R^5$ and $R^6$ together with the interjacent nitrogen atom are a heterocyclyl group; and $R^7$ is hydrogen or alkyl group.

2. The method of claim 1 in which R is a phenyl group substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, hydroxy-$C_{1-4}$ alkyl, amino, $C_{1-4}$ alkanoyl, carbamoyl and $C_{1-4}$ alkylenedioxy groups.

3. The method of claim 2 in which $R^3$ and $R^4$ independently are hydrogen or halogen or a $C_{1-6}$ alkyl, $C_{1-6}$ alkoxy, $C_{3-8}$ cycloalkyl, phenyl or phenoxy group, which groups are optionally substituted by one or more substituents selected from halogen or phenyl groups.

4. The method of claim 3 in which $R^5$ and $R^6$ independently are hydrogen, a $C_{1-6}$ alkyl, $C_{1-6}$ alkoxy, $C_{3-8}$ cycloalkyl or phenyl group or a 5- or 6-membered heterocyclic ring or $R^5$ and $R^6$ together with the interjacent nitrogen atom represent a 5- to 6-membered heterocyclic ring, each group or ring being optionally substituted by one or more substituents selected from halogen atoms, cyano, $C_{3-6}$ cycloalkyl, halo-$C_{3-6}$ cycloalkyl and phenyl groups.

5. The method of claim 4 in which $R^7$ is hydrogen or a $C_{1-4}$ alkyl group.

6. A compound of the formula

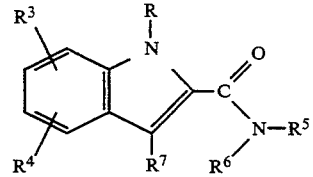

wherein R is nitrophenyl, cyanophenyl, hydroxyphenyl, hydroxymethylphenyl, aminophenyl, ethanoylphenyl, carbamoylphenyl, methylenedioxyphenyl, fluoro-methyl-phenyl, fluoro-methoxy-phenyl, fluoro-amino-phenyl, difluoro-amino-phenyl, chloro-amino-phenyl, dichloro-amino-phenyl, hydroxylmethoxy-phenyl, methyl-methoxy-phenyl, methyl-amino-phenyl, ethyl-amino-phenyl or dimethoxyphenyl group; $R^3$ is hydrogen, fluorine, chlorine or bromine or a methyl, ethyl, propyl, butyl, trifluoromethyl, methoxy, ethoxy, propoxy, butoxy, benzyloxy, cyclohexyl, phenyl or chlorophenoxy group; $R^4$ is hydrogen; $R^5$ is methyl, ethyl, propyl, butyl, trifluoroethyl, cyanomethyl, dichlorocyclopropylmethyl, benzyl, methoxy, cyclopropyl, cyclohexyl, phenyl or morpholinyl group; $R^6$ is hydrogen or a methyl, ethyl or propyl group; or $R^5$ and $R^6$ together with the interjacent nitrogen atom is an imidazolyl, piperidyl or morpholinyl group; and $R^7$ is hydrogen or a methyl group.

7. A compound according to claim 6 where R is 3,4-dimethyoxyphenyl.

8. The compound of the formula

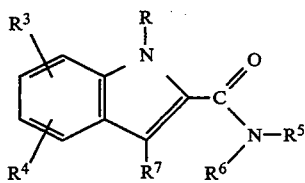

wherein R is 3,4-dimethoxyphenyl; $R^3$ and $R^4$ independently are hydrogen or halogen or an optionally substituted alkyl, alkoxy, cycloalkyl, phenyl or phenoxy group; $R^5$ and $R^6$ independently are hydrogen or an optionally substituted alkyl, alkoxy, cycloalkyl, phenyl or heterocyclyl group or $R^5$ or $R^6$ together with the interjacent nitrogen atom are a heterocycyl group; and $R^7$ is hydrogen or alkyl group.

9. A method which comprises a carrier and, as active ingredient, a compound of the formula

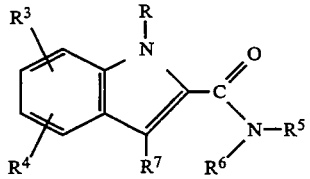

wherein R is nitrophenyl, cyanophenyl, hydroxyphenyl, hydroxymethylphenyl, aminophenyl, ethanoylphenyl, carbamoylphenyl, methylenedioxyphenyl, fluoro-methyl-phenyl, fluoro-methoxy-phenyl, fluoro-amino-phenyl, difluoro-amino-phenyl, chloro-amino-phenyl, dichloro-amino-phenyl, hydroxylmethoxy-phenyl, methyl-methoxy-phenyl, methyl-amino-phenyl, ethyl-amino-phenyl or dimethoxyphenyl group; $R^3$ is hydrogen, fluorine, chlorine or bromine or a methyl, ethyl, propyl, butyl, trifluoromethyl, methoxy, ethoxy, propoxy, butoxy, benzyloxy, cyclohexyl, phenyl or chlorophenoxy group; $R^4$ is hydrogen; $R^5$ is methyl, ethyl, propyl, butyl, trifluoroethyl, cyanomethyl, dichlorocyclopropylmethyl, benzyl, methoxy, cyclopropyl, cyclohexyl, phenyl or morpholinyl group; $R^6$ is hydrogen or a methyl, ethyl or propyl group; or $R^5$ and $R^6$ together with the interjacent nitrogen atom represent an imidazolyl, piperidyl or morpholinyl group; and R7 is hydrogen or a methyl group.

10. The method according to claim 9 wherein R is 3,4-dimethyoxyphenyl.

* * * * *